(12) United States Patent
Smith

(10) Patent No.: US 7,740,874 B2
(45) Date of Patent: Jun. 22, 2010

(54) METHOD OF MAKING A LANOLIN FREE ABSORPTION BASE

(75) Inventor: Thomas DeWitt Smith, Capistrano Beach, CA (US)

(73) Assignee: Quintessa Corporation, Capistrano Beach, CA (US)

(*) Notice: Subject to any disclaimer, the term of this patent is extended or adjusted under 35 U.S.C. 154(b) by 1823 days.

(21) Appl. No.: 10/670,378

(22) Filed: Sep. 26, 2003

(65) Prior Publication Data

US 2005/0192233 A1 Sep. 1, 2005

Related U.S. Application Data

(60) Provisional application No. 60/433,985, filed on Dec. 18, 2002.

(51) Int. Cl.
*A61K 8/02* (2006.01)
*A61L 15/16* (2006.01)
(52) U.S. Cl. ........................ 424/401; 424/444
(58) Field of Classification Search .......... 424/401, 424/444
See application file for complete search history.

(56) References Cited

U.S. PATENT DOCUMENTS

| 4,788,001 A | | 11/1988 | Narula | |
|---|---|---|---|---|
| 5,951,991 A | * | 9/1999 | Wagner et al. | 424/401 |
| 6,153,208 A | * | 11/2000 | McAtee et al. | 424/402 |

* cited by examiner

*Primary Examiner*—Sreeni Padmanabhan
*Assistant Examiner*—Renee Claytor
(74) *Attorney, Agent, or Firm*—Clark & Brody

(57) ABSTRACT

A composition of matter comprises a lanolin free absorption base. The absorption base in includes a superior lanolin free emulsifier selected for its HLB (hydrophilic-lipophilic balance) compatibility, neutral, nonionic absorption base ideal for the incorporation of many active ingredients. Use of this emulsifier permits low production temperatures during base manufacture, thereby allowing incorporation of heat labile active ingredients. More efficient emulsification is realized, which leads to a much lower concentration of emulsifier. The absorption base is especially effective formulation for hydrocortisone or its salts due to HLB compatibility, and stabilizing ingredients often found in prior art products can be eliminated due to HLB compatibility.

5 Claims, No Drawings

METHOD OF MAKING A LANOLIN FREE ABSORPTION BASE

This application claims priority under 35 USC 119(e) based on provisional application No. 60/433,985, filed on Dec. 18, 2002.

FIELD OF THE INVENTION

The present invention relates to a lanolin free absorption base and, in particular to an absorption base that comprises white petrolatum and a superior, lanolin free emulsifier, glucose based emulsifier such as methyl glucose dioleate. The absorption base can be combined with a preservative system and further diluted with water if desired. Other components can be added to the base as typically employed in the field of cosmetics.

BACKGROUND OF THE INVENTION

This invention relates generally to the field of cosmetics or cosmoceuticals and more specifically to a composition of matter comprising a lanolin free absorption base. An absorption base is a combination of specially selected ingredients, which must meet a number of criteria. They must first provide for the efficient emulsification of petrolatum and any subsequent addition of up to an equal amount of water to result in an elegant pharmaceutical or cosmetic base to be used alone or in combination with other ingredients. They must be safe and have wide consumer acceptance.

These bases have been the workhorses for maximum moisturization in hospital settings and as protective and clinically proven healing agents for skin conditions and burns.

An absorption base must first provide for the efficient emulsification of petrolatum (HLB 4) by an emulsifier. When there are large differences between the HLB for the petrolatum and the HLB the emulsifier larger amounts of an inferior emulsifier such as wool wax alcohols derived from lanolin are need and which may also necessitate the addition of stabilizing ingredients such as ceresin and or mineral oil.

The question of safety is always a concern in terms of liability. Animal products have generally been deemed safe in the United States as long as strict guidelines are followed. However, public perception may not always coincide with scientific fact. There is also the fact that some prior art products cannot pass a Draize (rabbit eye test) test for allergenicity or nonirritation. The invention (absorption base) components have been independently tested to be hypoallergenic and non-irritating as well as having a specifically selected preservative system for specific applications of the product (aqueous formulations). Additionally, while lanolin sensitivities are low in the general population, they increase dramatically in persons with various skin conditions.

It would seem obvious that the introduction of a new line of products derived from a more scientifically advanced approach to absorption bases is well overdue. The currently available analogous commercial products rely upon a cholesterized lanolin, also known as wool-wax alcohols (the most highly fractionated and allergenic component of lanolin) as the emulsifier for petrolatum to make an absorption base. An absorption base is petrolatum with the addition of an emulsifier such that, upon the addition of water, it will combine with water of an equal weight form a homogeneous and acceptable cosmetic or pharmaceutical end product. It can be used alone (or with the addition of water or other ingredients) for the purposes of providing an occlusive base for moisturization or for healing purposes or as a base for the inclusion of other active ingredients.

The dearth of emulsifiers available in the 1950's and a continuous commercial campaign allowed a single product to dominate and continue to produce and market a product virtually unchanged for half a century. Thus, the present day availability of many more emulsifiers and a better understanding of emulsification technology should allow for the introduction into the marketplace for superior absorption base products.

One problem facing the prior art is that lanolin based absorption bases must employ hardening agents, e.g., ceresin (beeswax) to avoid the separation of ingredients at even mildly elevated temperatures during normal use and must conversely employ a softening agent (mineral oil) to counteract the hardening of this type of product at cooler temperatures. Ceresin requires 65 degrees centigrade to melt and these temperatures can be problematic for the absorption base (degradation of the emulsifier) during the manufacturing process.

Another problem is that woolwax emulsifiers derived from lanolin are the most highly allergenic component of lanolin and may not be suitable for certain patient populations with pre-existing skin conditions.

SUMMARY OF THE INVENTION

The primary object of the invention is the creation of an effective and versatile absorption base that is not based on lanolin as the emulsifier.

A secondary objective is to eliminate the pervasive lanolin (sheep) smell found in products of this type.

Another object of the invention is increased consumer acceptance due to the ease of application at high or low temperatures of the product itself or products derived from this product.

Another object of the invention is reduction in manufacturing energy costs due to elimination of high melting components (ceresin requires 65 degrees centigrade to melt-invention requires only 50 degrees centigrade to melt), and decreases in labor costs due to fewer ingredients to manipulate and shorter production times as well as greater worker safety due to lower production temperatures.

Yet another object of the invention, is decreased raw materials cost due to elimination of unnecessary ingredients such as ceresin and mineral oil and a further reduced cost due the much smaller amounts of a more uniquely suited emulsifier for the emulsification of petrolatum to produce a superior product, the invention.

A further object of the invention is to decrease batch failure due to the "forgiving nature" of the product; the inventive product is stable over a wide range of manufacturing temperatures.

Still yet another object of the invention is increased safety profile due to selection of hypoallergenic, nonirritating ingredients.

Yet a further object of the invention is increased antimicrobial protection of products made due to compatible preservative system. Another object of the invention is increased consumer acceptance by eliminating "mad cow disease" concern of sheep products.

Other objects and advantages of the present invention will become apparent from the following descriptions taken in connection with the accompanying drawings, wherein, by way of illustration and example, an embodiment of the present invention is disclosed.

In one aspect of the invention, the invention is intended to cover the use of all non-lanolin based emulsifiers for the purpose of producing an absorption base, wherein the emulsifiers would fall within the range of 3 HLB units of the HLB value of petrolatum (HLB 4). Preferably, the emulsifier is any glucose-derived emulsifier that falls within this range. More preferably, the emulsifier is methyl glucose dioleate.

In accordance with a preferred embodiment of the invention, there is disclosed a composition of matter comprising a lanolin free absorption base using an effective amount of a superior lanolin free emulsifier, methyl glucose dioleate with white petrolatum. The emulsifier is selected for its HLB (hydrophilic-lipophilic balance) compatibility to efficiently emulsify the petrolatum resulting in a neutral, nonionic absorption base ideal for the incorporation of many active ingredients.

The absorption base can be made with low production temperatures, thus permitting the incorporation of heat labile active ingredients. In contrast to certain prior art emulsifier technology based on highly allergenic wool-wax alcohols, use of the above-referenced emulsifier leads to more efficient emulsification and a much lower concentration of emulsifier.

The absorption base is an especially effective formulation for hydrocortisone or its salts due to the HLB compatibility and elimination of unnecessary ingredients found in prior art product, also due to greater HLB compatibility.

DETAILED DESCRIPTION OF THE PREFERRED EMBODIMENTS

In one of aspect of the invention, the invention is intended to cover the use of all non-lanolin based emulsifiers for the purpose of producing an absorption base, wherein the emulsifiers would fall within the range of 3 HLB units of the HLB value of petrolatum (HLB 4). Preferably, the emulsifier is any glucose-derived emulsifier that falls within this range. More preferably, the emulsifier is methyl glucose dioleate.

In one mode, the invention comprises effective amounts of white petrolatum and the emulsifier described above to form a lanolin-free absorption base. The concentration range of the emulsifier is considered an effective amount in purpose of producing an absorption base. The absorption base can be used as is, or as one of skill in the art would use it, e.g., add other components to obtain a particular effect, see the modes and uses below. Preferably, the final concentration can range from 0.5% to up to 20% by weight, and preferred ranges of up to about 2.0% in a final diluted product.

In another mode, the absorption base can be modified by adding a preservative system. An example of a preferred preservative system is one under the Brand Name: Glydant Plus Details of the preservative system are as follows
Chemical Name: DMDM hydantoin (and) Iodo propynyl butyl carbamate
CAS numbers: 6440-58-0 and 55406-53-6
Activity spectrum: Broad spectrum, very effective fungicide
Type of compound: Nonionic cyclic and nonionic acyclic
Use concentration: 0.04-0.25%
Solubility: Soluble in surfactants, alcohols, glycols
Optimum pH: 3-9
Stability: Stable over a wide pH range and temperature up to 80° C.
Compatibility/Inactivation: No compounds known to be incompatible
Toxicity: Components of Glydant Plus have been the subject of extensive toxicological testing. The studies indicate that these components are safe and present minimal hazards at recommended use levels.
Regulatory status: Both ingredients are EPA registered.
Supplier: Lonza, see Cosmetics Preservatives *Encyclopedia* Antimicrobials, page 60, Vol. 105, March, 1990. Allured Publishing Corp.

While this system is a preferred system, other systems that would function in a similar fashion could also be employed as part of the invention.

In yet a third mode, the preservative system-containing absorption base can be diluted with water to form yet another type of absorption base.

An exemplary methodology of making the three modes described above when using the preferred emulsifier methyl glucose dioleate is as follows.

Product Mode 1
1. Heat white petrolatum to 50 degrees centigrade
2. Add methyl glucose dioleate to the heated white petrolatum to achieve a 4% by weight final concentration for the base.
3. Mix until adequately combined, e.g., approximately 5 minutes.
4. May pour directly into final container to make absorption base brand name product (about 46 degrees centigrade).

Product Mode 2
1. Take the product from step (3) above and add a preservative system, e.g., DMDM hydantoin (and) Iodo propynyl butyl carbamate. The concentration of the preservative system can vary depending on the system. With the identified system, the concentration in weight percent should be around between 0.25 and 0.4% by weight.
2. Mix, if necessary, and pour directly into final container.

Product Mode 3
1. Take the product from step 1 of PRODUCT MODE 2 and add an equal amount of water that is preheated to 50 degrees centigrade.
2. Cool mixture to about 46 degrees centigrade
3. Pour into final container to make the MODE 3 product. Based on a 4% concentration of the emulsifier in the product of MODE 2, the final concentration of emulsifier in MODE 3 should be around 2% by weight.

It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The knowledge of emulsification and the making of an absorption base are well-known. However, there appears to have been little attempt to create an absorption base using more modern and more well-suited emulsifiers. A composition of matter comprising a superior non-lanolin based emulsifier selected for its HLB (hydrophilic-lipophilic balance) compatibility with petrolatum to make an absorption base represents an advance in the safety, efficacy, and versatility of this class of agents.

New to this class of agents is an absorption base of non-animal origin and lacking the irritating and allergenic potential of it's competitor continuing to use 1950's technology by the use of highly allergenic (in some patient populations) wool-wax alcohols as the emulsifier for their products. Additionally, the neutral and nonionic nature of the formulation allows for a wide application as a pharmaceutical base while consumer acceptance has been increased by eliminating undesirable lanolin odors and making application (spreadability of the product to human skin) independent of ambient temperatures.

Notable to this new absorption base is the relative ease of manufacture. In the past, high temperatures had to be achieved to melt certain high melting temperature ingredients such as beeswax (unnecessary component in new absorption base). This resulted in the occasional overshoot of temperature limits, which would adversely affect lanolin-based emulsifiers (cracking of emulsion). Additionally, these high temperatures resulted in long wait times for the cooling down of the mixture before an optimum pour temperature could be reached. Prolonged cooling down times of variable duration can lead to variations in the end product and lack of uniformity between batches. In the new absorption base, high operating temperatures do not exceed that which would be perceived as more than warm to the touch (50 degrees centigrade) and thus, increasing worker safety, reducing labor costs and energy costs. Pour temperature (container filling) of the new absorption base is only about 46 degrees centigrade (4 degrees lower than mixing temperature) vs. 19 degrees centigrade difference of prior art bases (assuming melting temperature of beeswax of 65 degrees centigrade and same pour temperature of 46 degrees centigrade). Thus, the invention leads to overall lower production costs by actually eliminating what are now unnecessary ingredients.

Operational temperatures may be as low as 50° C. (melting point range of white petrolatum is around 49+° C., and up to 60° C., depending on the particular grade being used) or may be as high as 80° C. without a significant degradation of the final product.

Commercial success over the prior art bases depends on expanding the applications for a new invention. The new absorption base is ideal for the efficient incorporation of many active drug ingredients and is especially suited for the effective incorporation of hydrocortisone or it's salts (HLB 6) due to the compatibility of the emulsifier (HLB 5) up to a concentration of hydrocortisone of 10% or greater. Additionally, the new absorption base is useful for the incorporation of heat labile active ingredients due to lower manufacturing temperatures.

Other applications for the absorption base include its use as a superb vehicle for the delivery of sunscreen ingredients for the heavy duty use by the military, lifeguards, skiers, etc. The absorption base can incorporate anti-aging ingredients such as are commonly used in the industry.

Other features of the invention include:
1. A composition of matter comprising a lanolin free absorption base with superior lanolin free emulsifier selected for HLB (hydrophilic-lipophilic balance) compatibility.
2. Neutral, nonionic absorption base ideal for the incorporation of many active ingredients.
3. Low production temperatures allows incorporation of heat labile active ingredients.
4. Competitor uses 1950's emulsifier technology based on highly allergenic wool-wax alcohols.
5. More efficient emulsification leads to much lower concentration of emulsifier.
6. Especially effective formulation for hydrocortisone or its salts due to HLB compatibility.
7. Elimination of stabilizing ingredients in competitor product due to HLB compatibility.

In conclusion, the invention of a new absorption base addresses a broad spectrum of issues ranging from manufacturing problems, allergenicity and contamination of animal based products to limitations of applications and consumer acceptance of the end product. The invention has improved upon all of these concerns.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A method of making an emulsified absorption base comprising:
   a) heating white petrolatum up to 80° C.; and
   b) adding an effective amount of methyl glucose dioleate to the white petrolatum and mixing the two components together to form an absorption base; and
   c) diluting the absorption base with water preheated to up to 50° C. to form the emulsified absorption base for skin use alone or skin use when the emulsified absorption base is combined with other ingredients.

2. The method of claim 1, further comprising adding a preservative system to the absorption base to form a preservative system-containing absorption base.

3. The method of claim 1, further including adding an effective amount of a hydrocortisone or a hydrocortisone salt to the absorption base.

4. The method of claim 2, wherein the preservative system is DMDM hydantoin and Iodo propynyl butyl carba mate.

5. The method of claim 2, further including adding an effective amount of a hydrocortisone or a hydrocortisone salt to the absorption base.

* * * * *